US012712073B2

(12) United States Patent
Claude et al.

(10) Patent No.: US 12,712,073 B2
(45) Date of Patent: Aug. 18, 2026

(54) SYSTEM FOR MANAGING ENDODONTIC DATA

(71) Applicant: MICRO-MEGA INTERNATIONAL, Besancon (FR)

(72) Inventors: Stéphane Claude, La Roche (CH); Marie Devalloir, Besancon (FR)

(73) Assignee: MICRO-MEGA INTERNATIONAL, Besancon (FR)

( * ) Notice: Subject to any disclaimer, the term of this patent is extended or adjusted under 35 U.S.C. 154(b) by 145 days.

(21) Appl. No.: 18/570,716

(22) PCT Filed: Jun. 15, 2022

(86) PCT No.: PCT/EP2022/066425
§ 371 (c)(1),
(2) Date: Dec. 15, 2023

(87) PCT Pub. No.: WO2022/263575
PCT Pub. Date: Dec. 22, 2022

(65) Prior Publication Data

US 2024/0282438 A1 Aug. 22, 2024

(30) Foreign Application Priority Data

Jun. 16, 2021 (FR) ...................................... 2106382

(51) Int. Cl.
*G16H 40/40* (2018.01)
*A61C 5/40* (2017.01)
*G06F 21/60* (2013.01)

(52) U.S. Cl.
CPC ............... *G16H 40/40* (2018.01); *A61C 5/40* (2017.02); *G06F 21/602* (2013.01); *A61C 2204/005* (2013.01)

(58) Field of Classification Search
CPC .... G16H 40/40; A61C 5/40; A61C 2204/005; G06F 21/602; H04L 63/08; H04L 63/12
See application file for complete search history.

(56) References Cited

U.S. PATENT DOCUMENTS

2009/0205820 A1* 8/2009 Koederitz ............. E21B 19/165 166/250.01
2020/0043604 A1* 2/2020 Singh ....................... G06N 5/02
(Continued)

FOREIGN PATENT DOCUMENTS

EP 3699923 A1 8/2020
WO WO-2018118415 A1 * 6/2018 ............ A61B 34/35

OTHER PUBLICATIONS

Yazid, Nur Athirah. "Development of automated visual tracking system for surgical instruments." Thesis—Master of Engineering (Biomedical). University of Malaya. 2016 (Year: 2016).*
(Continued)

*Primary Examiner* — Linh Giang Le
(74) *Attorney, Agent, or Firm* — Maier & Maier, PLLC

(57) ABSTRACT

A system for managing data of an environment of an endodontic instrument, which includes: an endodontic instrument, intended to experience several stages of the life cycle such as logistics, use during endodontic treatment, end of life, the instrument being equipped with a unique identifier, and presenting recommended use parameters; an element for obtaining at least one real usage parameter experienced by the instrument during a life cycle stage; an element for reading the unique identifier during at least one stage of the life cycle of the instrument; computer equipment intended to be connected to the reading element and the obtaining element, including a database, and executing a computer program. The computer program is configured to record in the database, during at least one life cycle step, the (Continued)

unique identifier of the instrument read, the actual usage parameter obtained, a timestamp, and this recording is authenticated.

15 Claims, 1 Drawing Sheet

(56) References Cited

U.S. PATENT DOCUMENTS

2020/0395118 A1* 12/2020 Codd ..................... G16H 40/40
2021/0064605 A1* 3/2021 Bálint ................... H04W 12/35

OTHER PUBLICATIONS

International Search Report issued on Sep. 29, 2022, in corresponding International Patent Application No. PCT/EP2022/066425, 7 pages.

* cited by examiner

[Fig. 1]
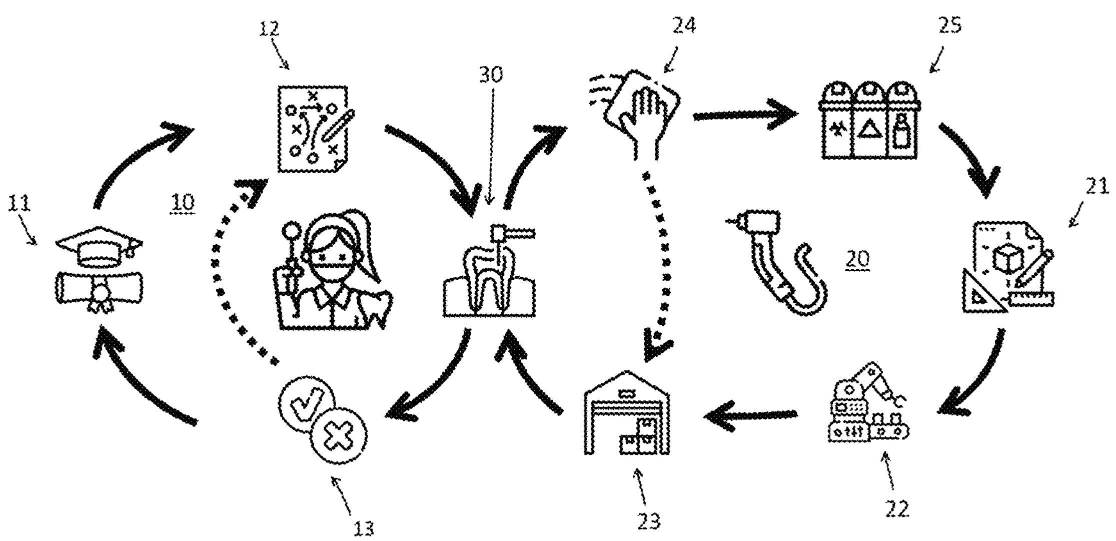
[Fig. 2]
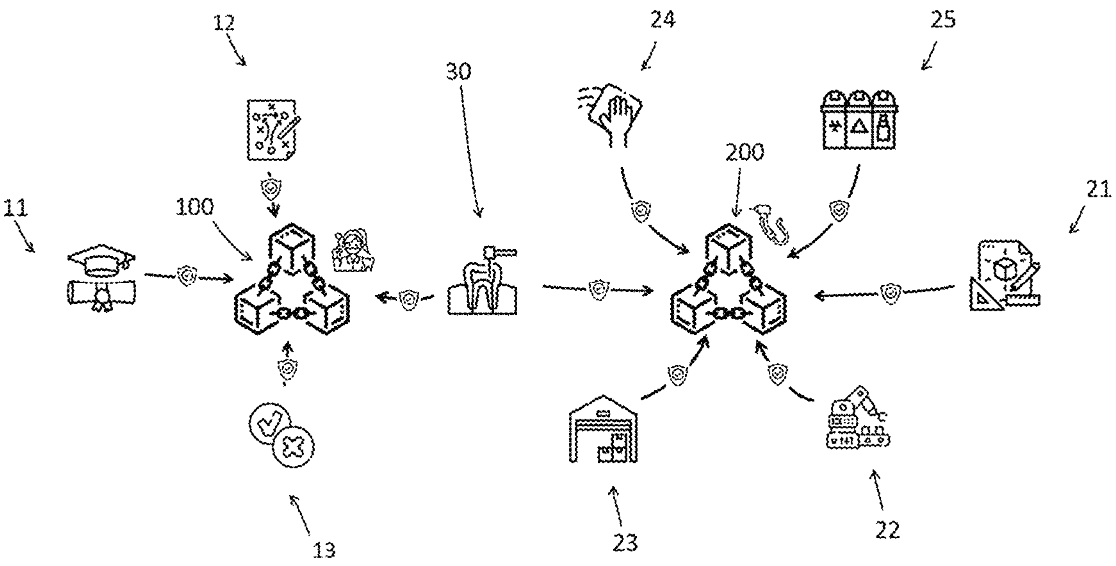

SYSTEM FOR MANAGING ENDODONTIC DATA

FIELD

The invention relates to the technical field of endodontics, and in particular that of the prevention of incidents in the endodontic field.

BACKGROUND

In the field of endodontics, breakage of the instrument used to carry out the care treatment is a frequent complication. Its systematic consequence is an extension of the time necessary to carry out the surgical act. Above all, the complications are clinical:

- in the case where it is possible to recover the broken portion of the instrument, the consequence is a weakening of the tooth by a reduction in the residual wall thickness;
- in the case where it is not possible to recover the broken portion, an infection might appear in its vicinity, which will result in the extraction of the tooth.

The occurrences of instrument breakages are generally reduced by the design of root canal instruments, to make them more resistant to the stresses exerted during the endodontic treatment. However, breakage factors are not only limited to the characteristics of the instrument: the way the practitioner uses it also has a major impact. Hence, the preventive actions undertaken at the instrument design step are not enough.

In order to limit the overloads exerted by the practitioner, some handpieces, driving the instrument, are equipped with devices for controlling the torque exerted by the motor on the instrument, or enable a real-time measurement of the operating parameters of the instrument. However, in the case of reusable instruments, this type of instantaneous measurements cannot prevent other types of ruin, such as fatigue breakages.

Moreover, the instruments might be weakened by stresses other than mechanical, for example thermal stresses. A reusable instrument must be sterilized under specific time and temperature conditions in order not to degrade its mechanical characteristics. Some instruments are not reusable and should not even be sterilized otherwise they will lead to a certain ruin.

Finally, in the event of an instrument breakage, it is quite difficult to accurately know what happened. The information is collected on the basis of statements, they cannot therefore be verified. What is more, the practitioner could have purchased the equipment from a reseller, which further complicates the transmission of information between the practitioner and the manufacturer of the equipment. Hence, the analysis of the causes having led to the incident is difficult.

Yet, the regulatory compliance of an instrument is based on avoiding failures of the instrument during normal use thereof. For the manufacturer of the instrument, it is therefore essential to know whether the failures are due to a misuse, and where appropriate, to be able to prove it with certainty.

Moreover, the collected information could also be used in the context of a clinical study. But reporting information that is not reliable will be considered unacceptable by the competent authorities.

Finally, a patient should be able to trust his/her practitioner. Yet, a patient does not have effective or reliable means for verifying the know-how or the training level of the practitioner who will perform an endodontic gesture.

SUMMARY

The invention aims to overcome the drawbacks of the prior art, in particular by providing an endodontic data management system allowing analyzing and preventing instrumental breakage, while taking the largest possible number of its occurrence factors into account.

The invention also aims to provide a data management system allowing obtaining information reports that are reliable, and possibly have a probative force, whether this information is intended for clinical studies or for regulatory compliance analyzes.

The invention also aims to be able to guarantee the training level of a practitioner with regards to an endodontic gesture to be performed.

To this end, a system for managing data of an environment of an endodontic instrument has been developed.

According to the invention, the system comprises:

- an endodontic instrument, intended to undergo a number of life-cycle steps such as a logistical step, a step of use to provide endodontic care treatment, an end-of-life step, the instrument being equipped with a unique identifier, and having recommended use parameters;
- means for obtaining at least one real use parameter to which the instrument is subjected during a life-cycle step;
- means for reading the unique identifier during at least one life-cycle step of the instrument;
- a piece of computer equipment intended to be connected to the reading means and the obtaining means, comprising a database, and executing a computer program.

According to the invention, the computer program is configured to record in the database, during at least one life-cycle step, the read unique identifier of the instrument, the obtained real use parameter, a timestamp, and this record is authenticated.

In this manner, it is possible to accurately know the real use parameters that each instrument has undergone, and therefore how it has been used, stored, cleaned, etc., during at least one step of its life cycle. In the event of a ruin, this allows easily knowing whether it is due to a failure caused by the instrument, by a misuse, or by poor logistics.

Moreover, the data collected allow making the design of instruments more reliable, in order to make them more resistant and more durable, or adapting the use recommendations to the performances actually obtained.

In turn, the authentication as well the timestamping ensure that the data are not altered or modified during recording, collection and analysis thereof. The data is secure and protected against tampering. Hence, the data can be used in the context of clinical studies. They also have the expected probative force to prove a misuse.

The invention also relates to a system for managing data of an endodontic environment, comprising:

- an endodontic instrument intended to cooperate with a piece of endodontic equipment, the instrument being equipped with a means for identifying the instrument type;
- information relating to the obtainment, by the practitioner, of a certificate of competence to use the instrument type with the equipment, issued by a training organization;
- the piece of endodontic equipment comprising means for reading the identifier of the instrument;

a piece of computer equipment connected to the piece of endodontic equipment and intended to receive the read information of the identifier and the information relating to the obtainment of the certificate of competence by the practitioner, the piece of computer equipment executing a computer program.

According to the invention, the computer program is configured to verify and record in a database a match between the information relating to the identified instrument type, the ability of the practitioner to use this instrument type with the equipment, and this record is authenticated.

In this manner, the invention allows ensuring that the practitioner is qualified for the care treatment he/she is about to carry out, each instrument type being dedicated to a care treatment type. Hence, the risks of misuse are considerably reduced, and even eliminated. In the event of a ruin, this allows facilitating knowing whether it is due to a failure caused by the instrument or caused by a misuse.

The effects provided by authentication in the context of this second invention are similar to those mentioned before. In particular, the competence of the practitioner can be proven, which reinforces the trust that the patient places in him/her.

Hence, each of these two solutions provides a response to the problem of endodontic incidents and instrument breakages, since each of these solutions allows addressing one of the two major causes of these breakages: the intrinsic failure of the instrument and the misuse (including poor logistics). These two solutions are based on the same general concept of collecting endodontic data, for measurement and prevention purposes.

In a particular embodiment, the piece of computer equipment is intended to receive information relating to endodontic care treatment, and the computer program is configured to verify and record the adequacy between the information relating to the care treatment to be carried out, the piece of endodontic equipment and the instrument used. Thus, depending on the care treatment to be performed and the corresponding sequence, if the practitioner uses the wrong equipment or instrument, the piece of computer equipment is able to alert the practitioner. In any case, this information is recorded and authenticated.

Advantageously, the piece of computer equipment is intended to receive information relating to the clinical outcomes of the endodontic care treatment, and the computer program is configured to take a clinical result of the treatment into account for continuous improvement purposes, for example to improve trainings provided by the organization, or to update a training schedule of the practitioner, or to improve the design of the instrument or of the piece of endodontic equipment. Depending on the probable cause of failure identified by the program, the information relating to the clinical outcomes is sent to the training organization and/or to the manufacturer of the instrument or of the piece of endodontic equipment.

To make the collected information reliable and obtain tangible information regarding the occurrences of misuses, the computer program is configured to verify and record a discrepancy between the recommended use parameters and the obtained real use parameters, and this record is authenticated.

In order not to let a misuse occur, the management system comprises a piece of endodontic equipment intended to receive the instrument, such as a handpiece, and the computer program is configured to adapt the operation of the piece of equipment according to the obtained real use parameter.

Still for clinical safety, the database contains a list of types of instruments compatible with the piece of endodontic equipment, and the computer program is programmed to identify the instrument type from the read unique identifier, in order to verify the compatibility of the instrument with the piece of equipment. By compatibility, it should herein be understood the possible adequacy between the intended use parameters and the operating parameters that the piece of endodontic equipment can adopt.

For the same purpose, the piece of computer equipment is intended to receive information relating to the care treatment to be performed, and the computer program is programmed to identify the instrument type from the read unique identifier, in order to verify the compatibility of the instrument with the care treatment to be performed. By compatibility, it should herein be understood that the instrument is well suited to a given step in the treatment sequence.

In practice, the computer program is, for example, programmed to:

- search within a first table of a database for the read unique identifier, in order to detect which instrument model will be used; then
- select within a second table the care treatments for which this instrument model has been designed; and
- verify the correspondence between the care treatment to be performed and the care treatments for which this instrument model has been designed:
- if the care treatment to be performed corresponds to the care treatments for which this instrument model has been designed, the program outputs valid output data;
- if the treatment to be performed does not correspond to the care treatments for which this instrument model has been designed, the program outputs invalid output data, i.e. it records the defect within the database data, and/or emits an alarm.

Advantageously, the computer program is able to estimate a lifespan before breakage of the instrument based on real use parameters. In this manner, it is possible to use the instrument for as long as possible in order to amortize its cost, but not to go as far as ruin thereof.

In a preferred embodiment, the life-cycle steps include several steps among use, reuse, storage and transportation, and preferably all of these steps. Thus, as many steps as possible that could have an impact on the lifespan of the instrument are monitored, so that the risk of missing an event likely to lead to the ruin of the instrument is reduced.

Preferably, the piece of computer equipment is intended to receive information relating to aging of the instrument, such as wear thereof or its mechanical characteristics, at the end-of-life step. This information enables the manufacturer to verify the validity of its design models, and to carry on its continuous improvement process.

The instrument type identifier or the unique identifier of the instrument and the means for reading use, for example, radio-frequency identification technologies, and preferably by ultra-high frequency RFID protocol. Thus, the identifier can be read remotely, and it is possible to mass read the identifiers of several instruments stored together, for example in stock.

In order to be reliable and to provide access to the sequence of the records, the authentication of the records uses a blockchain encryption, so-called "blockchain" in English.

BRIEF DESCRIPTION OF THE DRAWINGS

FIG. 1 is a block diagram illustrating the general concept combining together a preferred embodiment of the two inventions.

FIG. 2 is a diagram illustrating the authenticated recording of data in the context of the general concept combining together these two embodiments.

DETAILED DESCRIPTION

Referring to the diagram of FIG. 1, the two solutions objects of the invention are combined together by the general concept of traceability and data acquisition in an endodontic context.

Preferably, this acquisition is performed for several steps, which allows reinforcing the credibility of the reported information, and having more elements to analyze these data.

The diagram includes two life cycles:

a first cycle (10) relates to the practitioner, and in particular to the assessment of his ability to carry out some care treatments. The first cycle (10) illustrates the continuing training (11), preparation of a care treatment (12), use of an instrument (30), post-treatment monitoring (13) steps;

a second cycle (20) relates to the instrument, and in particular to its evolution throughout different steps of its service life. The second cycle (20) illustrates different design (21), manufacturing (22), storage (23), use (30), reuse (24) and recycling (25) steps.

The two life cycles (10, 20) have the step (30) in common, during which the instrument is used to carry out a care treatment. It is during this step that endodontic incidents might occur, and the causes of which might need to be investigated on the of the practitioner side, therefore in the first cycle (10), or on the instrument side, therefore in the second cycle (20).

As regards the first cycle (10), the first step to be described is the continuing training step (11) of the practitioner. Practitioners have a legal obligation to train throughout their career, after obtaining their diploma. This training is completed with an authorized training organization, such as a faculty, and the organization can issue a certification or certificate of training or competence.

The training may cover how to carry out some care treatments, i.e. the particular gestures to be performed. In other cases, the training may cover the use of particular instruments. It is assumed that an instrument is designed for carrying out a particular care treatment, and that there is a correlation between a care treatment and an instrument.

Finally, the training may cover the piece of endodontic equipment receiving the instrument. This may consist of a handpiece the settings of whose speed, torque and reciprocity parameter are different, or should be adapted according to the instrument. For readability, only training in the use of the instrument is described, but throughout the entire document, it should be understood that the practitioner could be trained in the use of an instrument, a piece of endodontic equipment, or the completion of a gesture.

According to the invention, the certificate of competence issued by the training organization, or the information according to which the certificate has been issued, is recorded in an authenticated manner. In a preferred embodiment, this authenticated record uses blockchain encryption technology, so-called "blockchain" in English.

The blockchain allows keeping the data relating to the records, a timestamp of the time point when these records were performed, while being secure and authenticable.

Hence, the data relating to the first life cycle (10) are recorded progressively within a first blockchain (100) illustrated in the diagram of FIG. 2.

In order to execute the necessary computer programs, and to proceed with the computer data exchanges between the training organization and the practitioner wishing to keep his/her proofs of training, a piece of computer equipment is present at the practitioner and is intended to connect via a network to a piece of computer equipment of the training organization, for example via the internet.

Besides the training(s) followed by the practitioner in step (11), data relating to the care treatments to be performed by the practitioner are obtained during a care treatment preparation step (12). This preparation step (12) is based on clinical data available in a database of the piece of computer equipment.

These clinical data may be entered by the practitioner or originate from the medical file of the patient. These may consist of photographs, measurements, or an assessment made by the practitioner regarding the difficulty of the gesture to be performed. For example, depending on the geometry of the root canal to be treated, the practitioner could assign a difficulty on a scale from 1 to 5. The clinical data may also be the result obtained during a simulation of the care treatment to be performed, either on a computer model or on a replica of the tooth to be treated and obtained by 3D printing.

These clinical data are used in order to determine the type of endodontic care treatment to be performed. The decision may be made by the practitioner himself/herself, or by a computer program executed by the piece of computer equipment, and which offers one or more treatment(s) that could correspond to the diagnosis made by the practitioner.

Preferably, this preparation step (12) also allows verifying that the particular care treatment to be performed actually falls within the area of expertise of the practitioner, according to the trainings completed during the continuing training step (11). This preparation step (12) also allows knowing which processing sequence should be executed, and possibly ordering the instruments necessary to perform this sequence.

In practice, the computer program is, for example, programmed to:

search within a first table of a database for the care treatments for which the practitioner has been trained, i.e. those for which he/she has obtained a certificate of competence;

verify the correspondence between the care treatment to be performed and the care treatments for which the practitioner has been trained:

if the care treatment to be performed corresponds to the care treatments for which the practitioner has been trained, the program outputs a valid output data;

if the care treatment to be performed does not correspond to the care treatments for which the practitioner has been trained, the program outputs an invalid output data, i.e. it records the fault within the database, and/or emits an alarm.

The data derived from the preparation step (12) are also recorded in an authenticated manner within the blockchain (100), so as to complete the information available for monitoring.

Once the care treatment to be performed has been properly prepared and the necessary equipment is available, the care treatment could then be performed in step (30). The practitioner should use the different instruments necessary for the treatment sequence. For example, for the treatment of a root canal, a treatment sequence may comprise:

opening the dental crown using a burr;

using an exploration file in order to determine the exact length of the canal to be treated;

a first shaping of the canal using a first small-size file;

a second shaping of the canal, and evacuating all of the remaining tissues using a larger second file;

sealing the canal using a gutta percha type gum.

The piece of endodontic equipment, herein the first and/or the second file, is equipped with means for reading an identifier carried by the instrument. This identifier allows recognizing the used instrument type. The identifier may be a barcode, a two-dimensional code such as a QR code or Datamatrix, or a radio-frequency identification transponder, so-called "RFID". Preferably, the used RFID protocol is based on ultra-high frequency standards as defined by the EPC UHF Gen2 standards by GS1 or the ISO 18000-6c.

Ultra-high frequency RFID, so-called "UHF RFID", allows reading codes remotely, without any direct visual access to the code. In addition, it allows mass reading, i.e. reading several codes at once, which is useful in some steps of the second life cycle (20) relating to the instrument.

Finally, UHF RFID protocols offer authentication solutions, which makes this technology particularly interesting in the context of the invention, where the traceability and the authentication of the records is essential.

Reading the identifier of the instrument by the piece of endodontic equipment allows knowing the received instrument type, for example the range of file used within the references of the manufacturer, as well as the dimensions of the file within this range.

Once the grasped instrument type is identified by the piece of endodontic equipment, the latter being connected to the piece of computer equipment, the computer program verifies:

firstly, whether the practitioner is able to perform the care treatment, according to the continuing training he/she has followed;

whether the instrument corresponds to the current endodontic treatment sequence, in order to avoid selection errors among the scheduled instruments.

Preferably, the piece of endodontic equipment comprises display means and the gestures to be performed during the care treatment are listed and suggested to the practitioner, with steps. Hence, the piece of endodontic equipment guides the practitioner throughout the treatment.

In practice, it is advantageous that the practitioner identifies himself/herself on the piece of computer equipment before carrying out the care treatment, for example with an identifier and a password. This allows easily managing staff changes within a practice, including when alternates or academics in training are present and provide care within the practice. It follows that each person has his/her own identifiers, so that the computer program is configured to verify and record in the database the adequacy between the competence of the practitioner in presence and the care treatment to be performed.

All of the information relating to the treatment is recorded and authenticated in the blockchain (100) relating to the practitioner, so that it is possible to ensure and have proof that the treatment has been carried out according to the recommendations of the manufacturers of the piece of endodontic equipment and of the instrument.

Following the care treatment, the practitioner can enter information relating to its progress and clinical outcomes, in a post-treatment monitoring step (13). The information may be entered immediately after the having carried out the care treatment, according to the findings of the practitioner. The information may also be entered a few days or weeks after having carried out the care treatment. Leaving a time limit for entering information allows knowing whether any complications have appeared following the care treatment, such as an infection for example.

This post-care monitoring information allows undertaking continuous improvement actions. It is possible that these actions are to be carried out for the practitioner, for example the continuing training he/she has received has not have allowed training him/her correctly, in which case the training organization needs to know this in order to update its training program.

Perhaps the provided training is correct but the practitioner has not assimilated it very well, in which case the continuous improvement actions will involve updating the training schedule of the practitioner.

The continuous improvement actions may also be intended for the manufacturer of the piece of endodontic equipment or of the instrument, for example if the practitioner notices that the expected performances or the operation of the equipment has not been achieved. In this case, it is the manufacturer of the piece of endodontic equipment or of the instrument who should receive this information in order to upgrade the design of the products.

The information from the post-treatment monitoring step (13) is also integrated into the blockchain (100), which allows recording it and authenticating it.

In practice, the computer program executes, for example, data analysis instructions (such as data mining, or analysis by artificial intelligence) in order to detect correlations between some failures and some use parameters (example: the rotational speed). In this manner, the computer program is configured to suggest scenarios of probable causes of misuse or of lack of knowledge to the training organization. Afterwards, the training organization can analyze these scenarios in order to improve the training it offers.

Similarly, the computer program executes, for example, data analysis instructions in order to detect correlations between some failures and some use parameters (example: the torque), or some characteristics of the instrument (example: the metal alloy used). In this manner, the computer program is configured to suggest scenarios of probable causes of misuse or of lack of knowledge the manufacturer. Afterwards, the manufacturer can analyze these scenarios in order to improve the design of the instruments.

Depending on the care treatment performed in step (30), information from the post-treatment monitoring step (13), and the regulatory training schedule of the practitioner, his/her training could be adapted within the training organization in order to guarantee that he/she completely masters the piece of endodontic equipment and the instruments, in order to eliminate any risk of misuse which could lead to clinical incidents or complications.

Of course, the practitioner performs several care treatments before returning to training. Hence, there are several successions of preparation (12), care (30) and post-treatment monitoring (14) steps before a new training step (11).

Hence, the first life cycle (10) relating to the practitioner is completed and each iteration of training, care treatment preparation, their completion and the post-treatment monitoring allows improving the progress of the next cycle. Thus, the risk of endodontic incidents, and in particular the risk of instrument breakage, is reduced.

In turn, the second solution object of the invention allowing solving the problem of endodontic incidents, and in particular of instrument breakage, focuses on an instrument.

The second life cycle (20) relating to the instrument includes a first design step (21), during which the manufacturer defines the geometry of the instrument, the materials forming it and any heat treatments. These characteristics will define recommended use parameters for the instrument to be able to operate safely and optimally in order to provide an accurate care treatment.

Before being put on the market, a new instrument undergoes validation phases during which the manufacturer will verify:

- its behavior during a care treatment;
- its mechanical strength in terms of bending, torsion, buckling, resistance to breakage and in particular fatigue breakages;
- its resistance to reuse procedures.

These data will enable the manufacturer to provide an instrument whose performances and lifespan are guaranteed when used according to the recommended use parameters.

In the case of a rotary instrument, these parameters will for example specify the rotational speeds and the acceptable maximum torques. If the rotation is done by alternating movements in one direction then in another, the angles in each direction will be specified.

The output data from the design step (21) are essentially the recommended use parameters, which are recorded in a database. Preferably, the data are recorded in an authenticated manner, by blockchain.

The next step of the second life cycle (20) is the manufacture (22) of the instrument, according to the defined design. In this step, the instrument is fitted with a unique identifier, or according to the English acronym "UDI" standing for "Unique Device Identification". The UDI allows knowing not only what type of instrument it is, but also, by access to the information in the database, its date of manufacture, possibly on which machine, from which raw material batch, when and which quality checks have been performed, etc.

All data from the manufacturing step (22) are recorded within a blockchain (200) relating to the instrument. In practice, the first block of the blockchain (200) is the block generated at the design step (21), so that the blockchain (200) carries the recommended use parameters. The second block is the block generated at the manufacturing step (22), with the manufacturing data and the UDI. Thus, each blockchain (200) of each instrument is rooted on their common design block, but each blockchain (200) is separated afterwards by a branch, or "fork" in English according to software terminology, so that each instrument has its own blockchain (200).

Preferably, at each step of the second life cycle (20), the data management system comprises means for obtaining real use parameters of the instrument. For example, obtaining the parameters can be done by measurement, using sensors, or by statement, using an interface between a user and a piece of computer equipment. This can be obtained by any suitable means allowing knowing to which real use parameters the instrument has been subjected, for example by computing means.

For example:

- the real use parameters at the manufacturing step (22) may include the grades of raw materials used, the results of quality controls performed, etc., and the obtaining means consist of a connection of the piece of computer equipment with the software or data management system of the manufacturer;
- the real use parameters at the use step (30) may include the mechanical stresses, and in the case of a rotary instrument the number of revolutions completed or the rotational speed and the jerks, the torque. They may also include the number of irrigations of the treated canal. Preferably, the obtaining means consist of suitable sensors within the piece of endodontic equipment receiving the instrument. In this case, the real use parameters are measured in real-time or continuously, i.e. at regular and short time intervals, for example every second, or every twenty-tenths of a second, or any other value suited to the needs of the desired resolution.

The real use parameters may be recorded when an event occurs, such as a quality check. They may be recorded in a discrete manner, such as a measurement of the temperature at some fixed time intervals. They may also be continuously monitored, so that only crossing of a threshold is recorded, such as an acceleration threshold which would reflect the occurrence of an impact.

Of course, the duration of exposure of the instrument to the real use parameters can be obtained. The comparison between the recommended use parameters and the real use parameters will allow verifying that the instrument is suitable for use during a care treatment.

It is obvious that in order to know the UDI of the monitored instrument, the piece of endodontic equipment comprises at least one means for reading the UDI, and preferably reading means are present at each step of the second life cycle (20).

After the manufacturing step (22), a storage step (23) takes place. It should be understood that this step covers all logistical operations which may include storage at the manufacturer, at the reseller, or at the practitioner, and the transport steps between each storage location.

During this storage step (23), the real use parameters correspond for example to the temperature, the pressure, the hygrometry, the acceleration to which the instrument is subjected. Indeed, depending on its design, the instrument may be particularly sensitive for example to temperature variations, so that storage in unsuitable conditions subjecting the instrument to temperatures varying from 20° C. to 50° C. in a repeated manner could affect its performances.

Hence, the real use parameters undergone in the storage step (23) are also recorded and authenticated in the blockchain (200) in order to be able to prove or incriminate the integrity of the instrument before use thereof.

The next step is the use (30) of the instrument, this step is common with the first life cycle (10) relating to the practitioner. The difference lies in that the second solution object of the invention requires a unique identifier of the instrument, because the question is no longer about knowing whether the practitioner is properly trained to use an instrument type, but knowing what the accurately used instrument has undergone in order to guarantee its resistance during the care treatment and to prevent breakage thereof.

It is during this use step (30) that the collection of real use parameters is most important. Indeed, depending on the mechanical loads applied to the instrument during the treatment, its lifespan is considerably affected: an instrument used for a difficult treatment, for example to treat a root canal whose trajectory comprises at least one right angle bending, could have its lifespan reduced to one single use, because this geometry exerts too much stresses on the instrument. On the other hand, the same instrument model used for simple treatments, for example straight root canals, may have a sufficient lifespan to perform several cares.

Hence, it is particularly relevant to acquire as much data as possible during the use of the instrument. In a preferred embodiment, the handpiece comprises a microcomputer executing a program, so that the handpiece trains the instrument, such as a file, and continuously adapts operation thereof according to the obtained real use parameter. This means that, if the file is overloaded, for example in torque, the program can choose to disengage the motor so as not to deteriorate the file.

In practice, the database contains the results of the aforementioned data analyses, so that typical situations likely to lead to ruin are known.

For example, these typical situations are defined by the number of prior uses of the instrument, by the accumulation of stresses that the instrument has undergone throughout the different steps of its life cycle.

When the real use parameters of the instrument correspond to an identified typical situation, then the program is programmed to modify the instrumental dynamics in order to get out of said typical situation. For example, this may consist in reducing the rotational speed, or stopping rotation.

Moreover, the computer program is configured to check and record a discrepancy between the recommended use parameters and the obtained real use parameters. For example, in the case where, despite the recommendations of the manufacturer, the practitioner choose to set the handpiece on rotational speeds or torques that are different from the recommended use parameters and likely to damage the instrument, this event will be recorded and authenticated.

In order to overcome these misuses, the piece of endodontic equipment comprises means for reading the UDI in order to be automatically configured according to the recommended use parameters, which are recorded in the database and/or in the blockchain (200).

For this same purpose, the computer program can be programmed to identify the instrument type from the read UDI, in order to verify the compatibility of the instrument with the piece of equipment. This means that, if an instrument intended to be used according to particular recommended use parameters is mounted in a piece of equipment that is unable to ensure these parameters, the computer program emits an alert on the piece of computer equipment. This alert is recorded and authenticated. For example, a file intended to be used with a reciprocating rotational movement should not be mounted on a handpiece that can deliver only a continuous rotational movement.

In practice, the computer program is, for example, programmed to:

- search within a first table of a database for the used instrument model, for example from the UDI;
- search within a second table of a database for the instrument models compatible with the piece of equipment;
- verify the correspondence between the instrument model and the piece of equipment:
- if the instrument model corresponds to the piece of equipment, the program outputs valid output data;
- if the instrument model does not correspond to the piece of equipment, the program outputs invalid output data, i.e. it records the fault within the database, and/or emits an alarm.

The practitioner might have several copies of each piece of endodontic equipment, for example several handpieces. In this case, each piece of equipment has its own identifier, and this identifier is also recorded in the database in order to be able to know with which piece of equipment the instrument has been used. This identifier does not need to be unique in the sense of a UDI, but it is necessary to be able to recognize the different copies held by the practitioner.

Like the other steps, the data relating to the use and the obtained real parameters are recorded and authenticated in the blockchain (200).

The next step of the second life cycle (20) is reuse (24). This step comprises all operations between the first use of the instrument and the next use thereof. In particular, yet without limitation, this consists in cleaning and sterilization of the instrument.

Indeed, these two operations are crucial for preventing the risk of infection: a poorly cleaned or poorly sterilized instrument is likely to carry germs originating from the first patient, and which will be transferred afterwards to the second patient.

Afterwards, the sterilization being performed in an autoclave, the instrument is subjected to a particular temperature cycle. Depending on the characteristics of the instrument, it may not be compatible with any sterilization cycle, in particular if the instrument itself has received a heat treatment. Subjecting an instrument to an incompatible sterilization cycle could degrade the mechanical characteristics of the instrument, so that the risk of instrument breakage during the subsequent use significantly increases.

This is why the reuse step (24) is the second most important step to monitor throughout the second life cycle (20).

The means for obtaining the real use parameters during the reuse step (24) may be of the declarative type, with manual entry by the practitioner on an interface, but the obtaining means preferably consist of sensors allowing accurately knowing the durations and the temperatures of the sterilization cycle, or the pH, the hygrometry, the intensity of the ultrasounds within an ultrasonic tank for cleaning.

Like the handpiece, the cleaning or sterilization equipment may be able to identify the instruments it receives, in order to verify their compatibility. For example, if a single-use instrument is mounted in an autoclave, the computer program is configured to emit an alert. This alert is recorded and authenticated.

By default, the number of reuses is defined by the manufacturer, according to the results obtained during the design phase (21). Each use of the instrument increments a counter recorded in the database, so that when the maximum number of uses is reached, the instrument is declared unfit by the computer program. This alert is recorded and authenticated.

In a preferred embodiment, the maximum number of uses of the instrument is defined by the computer program, based on the obtained real use parameters. Thus, depending on the loads imparted on the instrument during the treatments, the number of reuse operations performed, etc., the computer program evaluates the estimated lifespan of the instrument using a model or charts.

In this manner, as long as the computer program considers that the instrument can still withstand further use, the instrument remains in service. An instrument disposal alert is sent only when the index of confidence of survival at the next treatment is too low. This alert is recorded and authenticated.

In an advantageous embodiment, the model is automatically improved and updated by an artificial intelligence type processing algorithm. This algorithm uses and interprets all of the data collected about each instrument used by different practitioners, and can thus continuously improve the lifespan model of the instruments.

Nonetheless, should an instrument be broken or untwisted during a care treatment, the piece of computer equipment includes an interface to report the failure to the manufacturer of the instrument. In this manner, the information is submitted directly to the manufacturer without losses during the transmission of the information through several intermediaries.

In addition, the submitted information includes all of the data contained in the blockchain (200), which enables the manufacturer to have access to the entire life of the instrument, and all factors having influenced the early ruin thereof. The analysis of the data is facilitated.

Possibly, the piece of endodontic equipment is able to detect breakage or untwisting of the instrument, for example if the handpiece detects an instantaneous drop in the torque. Then, the computer program is programmed to automatically report the failure of the instrument, without any intervention from the practitioner. This report is recorded and authenticated. Thus, the manufacturer is sure to collect all occurrences of instrument failures, and not just those that are reported by diligent practitioners.

When the instrument can no longer be used, its end of life advantageously corresponds to a recycling step (25). Indeed, only the active portion of the instrument deteriorates during use, while the grip of the instrument, intended to mount the instrument on the piece of endodontic equipment, does not deteriorate. Hence, it is wise to reuse it, and to recycle the materials that cannot be used again.

Hence, this recycling step (25) includes the reverse logistics, consisting in returning the used instruments to the manufacturer, the operations of disassembling, cleaning and sterilizing the grips, then the release of the UDI within the database so that a new instrument could be fitted and a new blockchain (200) could be started.

During this recycling step (25), the manufacturer can also study the instruments that have been used. This may involve dimensional measurements to assess the actual wear of the instrument, mechanical tests such as bending or buckling measurements in order to verify how the mechanical characteristics of the instrument have evolved throughout its service life. It may also involve destructive tests, such as breakage tests, and in particular fatigue failure.

All this information relating to aging of the instrument, whether it has been used according to the recommended parameters or not, enables the manufacturer to validate its design models and carry on its continuous improvement process.

What is more, this information is also recorded and authenticated in the database, and the computer program is configured to update the predictive models and the lifespan charts of the instruments.

Throughout the life cycles (10, 20), recording the step or its number within the blockchain (100, 200) is not necessarily compulsory: the interpretation of the recorded data allows finding out at which step the record has been made:

- if the record originates from the training organization and relates to a certificate of competence, we know that this is the training step (11);
- if the record originates from a handpiece rotating the instrument, we know that this is the use step (30).

Preferably, the two solutions objects of the invention are deployed simultaneously, so that a practitioner has an unparalleled performance guarantee, because he/she has the assurance that his/her training is up to date and corresponds exactly to his/her needs, and because he/she has the assurance that the instruments he/she uses are monitored in order to prevent breakage thereof.

In the case where the two solutions objects of the invention are deployed simultaneously, the data management system is global and integrates the two life cycles (10, 20). Some computer equipment and some databases are shared.

Advantageously, the manufacturer of the instruments or of the piece of endodontic equipment, the training organization and practitioners can share data and access collected data in order to improve endodontic techniques and pursue the goal of reducing endodontic incidents.

Moreover, the data management system according to the invention may be designed differently from the diagrams and the detailed description without departing from the scope of the invention, which is defined by the claims. In particular, carrying out a care treatment and the reuse operations may be done in the same use step (30), and the piece of endodontic equipment may cover the handpieces receiving the instrument as well as the autoclaves or other cleaning equipment used for reuse, since deleterious misuses might occur in each case.

By computer equipment, it should be understood all hardware capable of executing a program, software or application, or the endodontic equipment part executing said programs and software. For example, the controller integrated into a handpiece is part of the computer equipment.

By computer program, it should be understood all programs, software or applications executed on the computer equipment. Hence, the computer program may include a multitude of subprograms executed at different locations and at different times within the data management system.

In general, the collected data are recorded in a database which is external to the endodontic instrument. Indeed, the data volume is too large to be stored in a memory contained in the instrument, for example in an RFID chip. Hence, the database is stored in a rewritable memory of the piece of computer equipment, preferably in a server connected to the Internet so that the manufacturer of the instrument could access the database remotely and in real-time.

In a variant which is not shown, a life cycle relates to the piece of endodontic equipment, and the collected data are integrated into a blockchain dedicated to the piece of equipment.

According to another variant which is not shown, a life cycle relates to the patient, and the collected data are integrated into a blockchain dedicated to his/her medical file.

Furthermore, all or part of the technical features of the above-mentioned different embodiments and variants may be combined with each other. Thus, the data management system of an endodontic environment may be adapted in terms of cost, functionalities and performance.

The invention claimed is:

1. A system for managing data of an environment of an endodontic instrument, wherein the system comprises:

- an endodontic instrument, intended to undergo a number of life-cycle steps, the instrument being equipped with a unique identifier, and the instrument having characteristics defining recommended use parameters;
- means for obtaining at least one real use parameter to which the instrument is subjected during a life-cycle step;
- means for reading the unique identifier during at least one life-cycle step of the instrument;
- a piece of computer equipment intended to be connected to the reading means and the obtaining means, comprising a database, and executing a computer program,
- wherein the computer program is configured to record in the database, during at least one life-cycle step, the read unique identifier of the instrument, the obtained real use parameter, a timestamp, and wherein this record is authenticated.

2. A system for managing data of an endodontic environment, wherein the system comprises:

an endodontic instrument intended to cooperate with a piece of endodontic equipment, the instrument being equipped with a means for identifying the instrument type;

information relating to an obtainment, by a practitioner, of a certificate of competence to use the instrument type with the equipment, the certificate of competence being issued by a training organization;

the piece of endodontic equipment comprising means for reading the identifier of the instrument;

a piece of computer equipment connected to the piece of endodontic equipment and intended to receive the read information of the identifier and the information relating to the obtainment of the certificate of competence by the practitioner, the piece of computer equipment executing a computer program, and wherein the computer program is configured to verify and record in a database a match between the information relating to the identified instrument type, the ability of the practitioner to use this instrument type with the equipment, and wherein this record is authenticated.

3. The data management system according to claim 2, wherein the piece of computer equipment is intended to receive information relating to the endodontic care treatment, and the computer program is configured to verify and record the match between the information relating to the care treatment to be carried out, the piece of endodontic equipment and the instrument used, and wherein this record is authenticated.

4. The data management system according to claim 2, wherein the piece of computer equipment is intended to receive information relating to the clinical outcomes of the endodontic care treatment, and the computer program is configured to take into account a clinic result of the treatment for the purposes of continuous improvement, for example to improve training offered by the organization, or to define a training plan for the practitioner, or to improve the design of the instrument or of the piece of endodontic equipment.

5. The data management system according to claim 1, wherein the computer program is configured to verify and record a difference between the recommended use parameters and the obtained real use parameters, this record is authenticated.

6. The data management system according to claim 1, wherein the data management system comprises a piece of endodontic equipment intended to receive the instrument, and the computer program is configured to adapt the operation of the piece of equipment according to the obtained real use parameter.

7. The data management system according to claim 1, wherein the database comprises a list of types of instruments compatible with the piece of endodontic equipment, and wherein the computer program is programmed to identify the instrument type from the read unique identifier, in order to verify the compatibility of the instrument with the piece of equipment.

8. The data management system according to claim 1, wherein the piece of computer equipment is intended to receive information relating to the treatment to be performed, and wherein the computer program is programmed to identify the instrument type from the read unique identifier, in order to verify the compatibility of the instrument with the care treatment to be performed.

9. The data management system according to claim 1, wherein the computer program is capable of estimating, based on the real use parameters, a lifespan before breakage of the instrument.

10. The data management system according to claim 1, wherein the life-cycle steps comprise several steps among use, reuse, storage and transport.

11. The data management system according to claim 1, wherein the piece of computer equipment is intended to receive information relating to the aging of the instrument, at the end-of-life step.

12. The data management system according to claim 1, wherein the unique identifier of the instrument and the reading means use radio-frequency identification technologies.

13. The data management system according to claim 1, wherein the authentication of the records uses blockchain encryption.

14. The data management system according to claim 2, wherein the identifier of the type of instrument and the reading means use radio-frequency identification technologies.

15. The data management system according to claim 2, wherein the authentication of the records uses blockchain encryption.

* * * * *